United States Patent
Doering et al.

(10) Patent No.: US 10,980,734 B2
(45) Date of Patent: Apr. 20, 2021

(54) ANTIPERSPIRANT PREPARATION

(71) Applicant: Henkel AG & Co. KGaA, Duesseldorf (DE)

(72) Inventors: Thomas Doering, Dormagen (DE); Gertraud Teckenbrock, Sprockhoevel (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 78 days.

(21) Appl. No.: 16/301,755

(22) PCT Filed: Apr. 24, 2017

(86) PCT No.: PCT/EP2017/059593
§ 371 (c)(1),
(2) Date: Nov. 15, 2018

(87) PCT Pub. No.: WO2017/202556
PCT Pub. Date: Mar. 30, 2017

(65) Prior Publication Data
US 2019/0282488 A1    Sep. 19, 2019

(30) Foreign Application Priority Data
May 23, 2016 (DE) .................. 10 2016 208 860

(51) Int. Cl.
*A61K 8/81* (2006.01)
*A61K 8/04* (2006.01)
*A61Q 15/00* (2006.01)
*A61K 8/58* (2006.01)
*A61K 8/891* (2006.01)

(52) U.S. Cl.
CPC ............ *A61K 8/8158* (2013.01); *A61K 8/046* (2013.01); *A61K 8/585* (2013.01); *A61K 8/891* (2013.01); *A61Q 15/00* (2013.01); *A61K 2800/30* (2013.01)

(58) Field of Classification Search
None
See application file for complete search history.

(56) References Cited

U.S. PATENT DOCUMENTS 5,830,440 A * 11/1998 Sturla ................. A61K 8/046
                                                    424/47
6,027,739 A *  2/2000 Nichols ................ A61K 8/73
                                                    424/401

FOREIGN PATENT DOCUMENTS

| DE | 102013225617 A1 | 6/2015 |
| DE | 102013225620 A1 | 6/2015 |
| WO | 9324105 A1 | 12/1993 |
| WO | 2015085998 A1 | 6/2015 |
| WO | 2016062507 A1 | 4/2016 |

OTHER PUBLICATIONS

EPO, International Search Report and Written Opinion issued in International Application No. PCT/EP2017/059593, dated Jun. 26, 2017.

* cited by examiner

*Primary Examiner* — Melissa S Mercier
(74) *Attorney, Agent, or Firm* — Lorenz & Kopf, LLP

(57) ABSTRACT

The present disclosure relates to an antiperspirant cosmetic agent containing:
a) from about 0.5 to about 7.0% by weight of at least one copolymer formed from the monomers
   i) N-tert-octylacrylamide
   ii) acrylic acid
   iii) tert.-butylaminoethyl methacrylate
   iv) and optionally further monomers
b) from about 40 to about 75% by weight of oil that is liquid at about 20° C. and about 1.013 hPa wherein the antiperspirant cosmetic agent does not contain any aluminium-containing compounds, use thereof, and methods using an agent of this kind.

19 Claims, No Drawings

ANTIPERSPIRANT PREPARATION

CROSS-REFERENCE TO RELATED APPLICATION

This application is a U.S. National-Stage entry under 35 U.S.C. § 371 based on International Application No PCT/EP2017/059593, filed Apr. 24, 2017 which was published under PCT Article 21(2) and which claims priority to German Application No. 10 2016 208 860.2, filed May 23, 2016, which are all hereby incorporated in their entirety by reference.

TECHNICAL FIELD

The present application relates to antiperspirant compositions having improved efficacy, and methods using these compositions.

BACKGROUND

In many cultural areas the cleaning of and caring for one's own body includes measures intended to counteract the development of an excess body odor considered to be unpleasant. The development of body odor is promoted, amongst other things, by perspiration, and therefore the cosmetics industry provides numerous toiletry products which have been developed for use in bodily regions having a high density of sweat glands, in particular in the armpit area. These toiletry products act in a sweat-inhibiting (antiperspirant) and/or deodorizing (deodorant) manner.

Cosmetic antiperspirants of the prior art usually contain at least one antiperspirant salt in addition to at least one oil or a fatty substance and an aromatic component or a perfume. The sweat-inhibiting salts used in these antiperspirants on the one hand reduce the sweat secretion of the body by employing a temporary constriction and/or blocking of the excretory ducts of the sweat glands, such that the amount of sweat can be reduced by approximately 20 to about 60%. On the other hand, they have an additional, deodorizing effect on account of their antimicrobial effect. Usually, activated basic aluminium and aluminium-zirconium halides are used as sweat-inhibiting salts. Furthermore, aluminium and aluminium-zirconium halides which are stabilized with organic acids as complex ligands can also be used. Humans with sensitive skin can react to sweat-inhibiting salts. The aluminium and aluminium-zirconium halides forming the basis of the use of antiperspirants can additionally build up visibly on the treated skin or on the textiles in contact with the treated skin, and in the case of textiles so too can residues of the cosmetic agent resistant to washing.

Aluminium-free antiperspirants and deodorants are described for example in German patent applications DE102013225617 A1 and DE102013225620 A1.

International application WO 93/24105 A1 describes aluminium-free antiperspirants on the basis of different water-insoluble polymers.

These and other aluminium-free antiperspirants, however, do not satisfy the increasing cosmetic requirements.

Against this background, the technical problem addressed by the present disclosure lies in providing an antiperspirant having a high efficacy against body odor, good skin compatibility, and a significantly reduced formation of residue on the skin and textiles. The antiperspirant should additionally be exemplified by high stability.

BRIEF SUMMARY

It has now surprisingly been found that the above-mentioned technical problems are solved by aluminium-free compositions which, in addition to a specific amphomeric polymer, also contain an oil. The present disclosure provides:

An antiperspirant cosmetic agent containing:
a) from about 0.5 to about 10% by weight of at least one copolymer formed from the monomers
   i) N-tert-octylacrylamide
   ii) acrylic acid
   iii) tert.-butylaminoethyl methacrylate
   iv) and optionally further monomers
b) from about 40 to about 75% by weight of oil that is liquid at about 20° C. and about 1.013 hPa wherein the antiperspirant cosmetic agent does not contain any aluminium-containing compounds.

The deodorizing cosmetic agent according to the preceding point, wherein the agent contains, as copolymer a), at least one copolymer formed from the monomers
   i) N-tert-octylacrylamide
   ii) acrylic acid
   iii) tert.-butylaminoethyl methacrylate
   iv) methyl methacrylate
   v) hydroxypropyl methacrylate.

The deodorizing cosmetic agent according to either one of the preceding points, wherein the copolymer a), in relation to the total weight of the agent, is contained in an amount of from about 1.0 to about 10% by weight, for example from about 3.0 to about 7.0% by weight.

The deodorizing cosmetic agent according to any one of the preceding points, wherein the oil is selected from the group of silicone oils, for example from the group of dialkyl and alkylaryl siloxanes, in particular from the group of cyclopentasiloxane, cyclohexasiloxane, dimethylpolysiloxane and methylphenylpolysiloxane.

The deodorizing cosmetic agent according to any one of the preceding points, wherein cyclopentasiloxane is contained as oil.

The deodorizing cosmetic agent according to any one of the preceding points, wherein the oil, in relation to the total weight of the agent, is contained in an amount of from about 25 to about 70% by weight, for example from about 35 to about 55% by weight.

The deodorizing cosmetic agent according to any one of the preceding points, wherein the cosmetic agent, in relation to the total weight of the agent, contains from about 10 to about 60% by weight, for example from about 15 to about 50% by weight, and in particular from about 20 to about 40% by weight of hydrophilic organic solvent.

The deodorizing cosmetic agent according to the preceding point, wherein the hydrophilic organic solvent is selected from the group of ethanol and propylene carbonate.

The deodorizing cosmetic agent according to any one of the preceding points, wherein the cosmetic agent, in relation to the total weight of the agent, contains from about 10 to about 50% by weight, for example from about 14 to about 46% by weight and in particular from about 18 to about 42% by weight of ethanol.

The deodorizing cosmetic agent according to any one of the preceding points, wherein the cosmetic agent, in relation to the total weight of the agent, contains from about 0.5 to about 4.0% by weight, for example from about 1.0 to about 3.5% by weight and in particular from about 1.5 to about 3.0% by weight of propylene carbonate.

The deodorizing cosmetic agent according to any one of the preceding points, wherein the agent has a vapour pressure (about 20° C.) of from about 1.0 to about 3.0 kPa, for example from about 1.2 to about 2.7 kPa, and in particular from about 1.4 to about 2.5 kPa.

The deodorizing cosmetic agent according to any one of the preceding points, wherein water is contained, in relation to the total weight of the agent, in amounts of less than about 5.0% by weight, preferably of less than about 3.0% by weight, and in particular of less than about 1.0% by weight.

The deodorizing cosmetic agent according to any one of the preceding points, wherein the agent, in relation to the total weight of the agent, contains from about 2.0 to about 20% by weight, for example from about 4.0 to about 16% by weight, and in particular from about 8.0 to about 12% by weight of at least one enzyme inhibitor.

The deodorizing cosmetic agent according to any one of the preceding points, wherein the agent contains an enzyme inhibitor from the group of trialkyl citric acid ester, preferably triethyl citrate or zinc glycinate, in particular triethyl citrate.

The deodorizing cosmetic agent according to any one of the preceding points, wherein the agent, in relation to the total weight of the agent, contains from about 0.5 to about 10% by weight, for example from about 1.0 to about 9.0% by weight, and in particular from about 4.0 to about 8.0% by weight of thickener.

The deodorizing cosmetic agent according to any one of the preceding points, wherein the agent contains a thickener from the group of hydrophobically modified silicates, for example from the group of hydrophobised hectorites, in particular from the group of hydrophobised hectorites with the INCI name Quaternium-18 Hectorite.

The deodorizing cosmetic agent according to any one of the preceding points, wherein the cosmetic agent, in relation to the total weight of the agent, consists to an extent of at least about 80% by weight, for example at least about 90% by weight, and in particular at least about 95% by weight of
  a) at least one copolymer formed from the monomers
    i) N-tert-octylacrylamide
    ii) acrylic acid
    iii) tert.-butylaminoethyl methacrylate
    iv) and optionally further monomers
  b) oil that is liquid at about 20° C. and about 1.013 hPa
  c) hydrophilic organic solvent
  d) enzyme inhibitor
  e) thickener.

A cosmetic preparation including
  i) deodorizing cosmetic agent according to any one of the preceding claims
  ii) propellant.

A cosmetic preparation including
  i) from about 10 to about 30% by weight of cosmetic agent according to any one of the preceding points
  ii) from about 70 to about 90% by weight of propellant.

A cosmetic product including
  a cosmetic agent or a cosmetic preparation according to any one of the preceding points
  a dispensing device having a spray valve.

Use of a deodorizing cosmetic agent, a cosmetic preparation, or a cosmetic product according to any one of the preceding points for preventing and/or reducing body odor.

A non-therapeutic cosmetic method for preventing and/or reducing body odor, in which a cosmetic agent according to any one of the preceding points is applied to the skin, in particular the skin of the armpits, and is left on the skin for at least about 1 hour, preferably for at least about 2 hours, preferably for at least about 4 hours, and in particular for at least about 6 hours.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

A first constituent of the antiperspirant cosmetic agent as contemplated herein is the copolymer a). With regard to the producibility, application properties and cosmetic effect of cosmetic compositions as contemplated herein, it has proven to be advantageous if the proportion by weight of the copolymer a) in the total weight of the agent is from about 1.0 to about 10% by weight, for example from about 3.0 to about 7.0% by weight.

The copolymer a) can be attributed to the monomers i) N-tert-octylacrylamide, ii) acrylic acid, iii) tert.-butylaminoethyl methacrylate and optionally further monomers.

Suitable copolymers a) include to an extent of at least about 90% by weight, for example at least about 95% by weight, and in particular at least about 97% by weight or even completely of the monomers N-tert-octylacrylamide, acrylic acid and tert.-butylaminoethyl methacrylate.

Particularly suitable are copolymers a) formed from the monomers i) N-tert-octylacrylamide, ii) acrylic acid, iii) tert.-butylaminoethyl methacrylate, iv) methyl methacrylate and v) hydroxypropyl methacrylate.

The previously described copolymers a) are for example sold under the name Amphomer® (INCI name: Octylacrylamide/Acrylates/Butylaminoethyl Methacrylate Copolymer; CAS number 70801-07-9) by the company National Starch.

A further subject matter of the present patent application is a cosmetic agent including at least one copolymer a) formed from the monomers
  i) N-tert-octylacrylamide
  ii) acrylic acid
  iii) tert.-butylaminoethyl methacrylate
  iv) methyl methacrylate
  v) hydroxypropyl methacrylate.

As second essential constituent b), the cosmetic agents contain from about 40 to about 75% by weight of oil that is liquid at about 20° C. and about 1.013 hPa. The term "oil" denotes substances that are immiscible with water.

Particularly suitable cosmetic agents contain at least one oil that is liquid at about 20° C. and about 1.013 hPa, from the group of
  esters of linear or branched saturated or unsaturated C2-30 fatty alcohols with linear or branched saturated or unsaturated C2-30 fatty acids,
  addition products of ethylene oxide and/or propylene oxide with mono or polyvalent $C_{3-22}$ alkanols
  dialkyl ethers and
  Paraffins. These oils have proven to be particularly effective in conjunction with the copolymer.

The use of oil from the group of silicone oils, for example from the group of dialkyl and alkylaryl siloxanes, in particular from the group of cyclopentasiloxane, cyclohexasiloxane, dimethylpolysiloxane, and methylphenylpolysiloxane is very particularly suitable, wherein cyclopentasiloxane is suitable in particular.

Deodorizing cosmetic agents according to any one of the preceding points, wherein the oil, in relation to the total weight of the agent, is contained in an amount of from about 25 to about 70% by weight, for example from about 35 to about 55% by weight.

The cosmetic agents do not contain any aluminium-containing compounds. The term "aluminium-containing compounds" is understood within the scope of the present disclosure to mean antiperspirant aluminium salts and aluminium-zirconium salts.

Suitable cosmetic agents, in addition to the oil, also contain hydrophilic organic solvent as further carrier.

A particularly advantageous cosmetic effect could be achieved with agents that contain, in relation to their total weight, from about 10 to about 60% by weight, for example from about 15 to about 50% by weight, and in particular from about 20 to about 40% by weight of hydrophilic organic solvent.

Suitable hydrophilic organic solvents are selected from the group of ethanol and propylene carbonate.

In the case of cosmetic agents containing ethanol, the ethanol content in the total weight of the agent is for example from about 10 to about 50% by weight, for example from about 14 to about 46% by weight, and in particular from about 18 to about 42% by weight. By contrast, the proportion by weight of the propylene carbonate in the total weight of suitable cosmetic agents is from about 0.5 to about 4.0% by weight, for example from about 1.0 to about 3.5% by weight, and in particular from about 1.5 to about 3.0% by weight propylene carbonate.

The cosmetic agents are preferably formulated with a low water content or are anhydrous. Suitable deodorizing cosmetic agents contain, in relation to the total weight of the agent, water in amounts of less than about 5.0% by weight, preferably of less than about 3.0% by weight, and in particular of less than about 1.0% by weight.

A technical parameter that has proven to be of relevance for the cosmetic effect of the agents as contemplated herein is the vapour pressure these agents. Cosmetically particularly advantageous cosmetic agents have a vapour pressure (about 20° C.) of from about 1.0 to about 3.0 kPa, preferably of from about 1.2 to about 2.7 kPa, and in particular of from about 1.4 to about 2.5 kPa auf.

The composition of a suitable cosmetic agent can be inferred from the following tables (values in % by weight in relation to the total weight of the cosmetic agent unless specified otherwise).

|  | Formula 1 | Formula 2 | Formula 3 | Formula 4 | Formula 5 |
|---|---|---|---|---|---|
| copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| optional additives | to 100 | to 100 | to 100 | to 100 | to 100 |

* formed from the monomers i) N-tert-octylacrylamide, ii) acrylic acid, iii) tert.-butylaminoethyl methacrylate and optionally further monomers

|  | Formula 6 | Formula 7 | Formula 8 | Formula 9 | Formula 10 |
|---|---|---|---|---|---|
| copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| optional additives | to 100 | to 100 | to 100 | to 100 | to 100 |

* formed from the monomers i) N-tert-octylacrylamide, ii) acrylic acid, iii) tert.-butylaminoethyl methacrylate, iv) methyl methacrylate und v) hydroxypropyl methacrylate

|  | Formula 11 | Formula 12 | Formula 13 | Formula 14 | Formula 15 |
|---|---|---|---|---|---|
| copolymer * | 0.5 to 10 | 0.5 to 10 | 1.0 to 10 | 1.0 to 10 | 3.0 to 7.0 |
| cyclopentasiloxane | 40 to 75 | 25 to 70 | 25 to 70 | 25 to 70 | 35 to 55 |
| optional additives | to 100 | to 100 | to 100 | to 100 | to 100 |

* formed from the monomers i) N-tert-octylacrylamide, ii) acrylic acid, iii) tert.-butylaminoethyl methacrylate and optionally further monomers

|  | Formula 16 | Formula 17 | Formula 18 | Formula 19 | Formula 20 |
|---|---|---|---|---|---|
| copolymer * | 0.5 to 10 | 0.5 to 10 | 1.0 to 10 | 1.0 to 10 | 3.0 to 7.0 |
| cyclopentasiloxane | 40 to 75 | 25 to 70 | 25 to 70 | 25 to 70 | 35 to 55 |
| optional additives | to 100 | to 100 | to 100 | to 100 | to 100 |

* formed from the monomers i) N-tert-octylacrylamide, ii) acrylic acid, iii) tert.-butylaminoethyl methacrylate, iv) methyl methacrylate und v) hydroxypropyl methacrylate

|  | Formula 21 | Formula 22 | Formula 23 | Formula 24 | Formula 25 |
|---|---|---|---|---|---|
| copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| hydrophilic organic solvent | 10 to 60 | 15 to 50 | 15 to 50 | 20 to 40 | 20 to 40 |
| optional additives | to 100 | to 100 | to 100 | to 100 | to 100 |

* formed from the monomers i) N-tert-octylacrylamide, ii) acrylic acid, iii) tert.-butylaminoethyl methacrylate and optionally further monomers

|  | Formula 26 | Formula 27 | Formula 28 | Formula 29 | Formula 30 |
|---|---|---|---|---|---|
| copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| hydrophilic organic solvent | 10 to 60 | 15 to 50 | 15 to 50 | 20 to 40 | 20 to 40 |
| optional additives | to 100 | to 100 | to 100 | to 100 | to 100 |

* formed from the monomers i) N-tert-octylacrylamide, ii) acrylic acid, iii) tert.-butylaminoethyl methacrylate, iv) methyl methacrylate und v) hydroxypropyl methacrylate

|  | Formula 31 | Formula 32 | Formula 33 | Formula 34 | Formula 35 |
|---|---|---|---|---|---|
| copolymer * | 0.5 to 10 | 0.5 to 10 | 1.0 to 10 | 1.0 to 10 | 3.0 to 7.0 |
| cyclopentasiloxane | 40 to 75 | 25 to 70 | 25 to 70 | 25 to 70 | 35 to 55 |
| hydrophilic organic solvent | 10 to 60 | 15 to 50 | 15 to 50 | 20 to 40 | 20 to 40 |
| optional additives | to 100 | to 100 | to 100 | to 100 | to 100 |

* formed from the monomers i) N-tert-octylacrylamide, ii) acrylic acid, iii) tert.-butylaminoethyl methacrylate and optionally further monomers

|  | Formula 36 | Formula 37 | Formula 38 | Formula 39 | Formula 40 |
|---|---|---|---|---|---|
| copolymer * | 0.5 to 10 | 0.5 to 10 | 1.0 to 10 | 1.0 to 10 | 3.0 to 7.0 |
| cyclopenta-siloxane | 40 to 75 | 25 to 70 | 25 to 70 | 25 to 70 | 35 to 55 |
| hydrophilic organic solvent | 10 to 60 | 15 to 50 | 15 to 50 | 20 to 40 | 20 to 40 |
| optional additives | to 100 | to 100 | to 100 | to 100 | to 100 |

* formed from the monomers i) N-tert-octylacrylamide, ii) acrylic acid, iii) tert.-butylaminoethyl methacrylate, iv) methyl methacrylate und v) hydroxypropyl methacrylate

|  | Formula 41 | Formula 42 | Formula 43 | Formula 44 | Formula 45 |
|---|---|---|---|---|---|
| copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| ethanol | 10 to 60 | 15 to 50 | 15 to 50 | 20 to 40 | 20 to 40 |
| optional additives | to 100 | to 100 | to 100 | to 100 | to 100 |

* formed from the monomers i) N-tert-octylacrylamide, ii) acrylic acid, iii) tert.-butylaminoethyl methacrylate and optionally further monomers

|  | Formula 46 | Formula 47 | Formula 48 | Formula 49 | Formula 50 |
|---|---|---|---|---|---|
| copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| ethanol | 10 to 60 | 15 to 50 | 15 to 50 | 20 to 40 | 20 to 40 |
| optional additives | to 100 | to 100 | to 100 | to 100 | to 100 |

* formed from the monomers i) N-tert-octylacrylamide, ii) acrylic acid, iii) tert.-butylaminoethyl methacrylate, iv) methyl methacrylate und v) hydroxypropyl methacrylate

|  | Formula 51 | Formula 52 | Formula 53 | Formula 54 | Formula 55 |
|---|---|---|---|---|---|
| copolymer * | 0.5 to 10 | 0.5 to 10 | 1.0 to 10 | 1.0 to 10 | 3.0 to 7.0 |
| cyclopenta-siloxane | 40 to 75 | 25 to 70 | 25 to 70 | 25 to 70 | 35 to 55 |
| ethanol | 10 to 60 | 15 to 50 | 15 to 50 | 20 to 40 | 20 to 40 |
| optional additives | to 100 | to 100 | to 100 | to 100 | to 100 |

* formed from the monomers i) N-tert-octylacrylamide, ii) acrylic acid, iii) tert.-butylaminoethyl methacrylate and optionally further monomers

|  | Formula 56 | Formula 57 | Formula 58 | Formula 59 | Formula 60 |
|---|---|---|---|---|---|
| copolymer * | 0.5 to 10 | 0.5 to 10 | 1.0 to 10 | 1.0 to 10 | 3.0 to 7.0 |
| cyclopenta-siloxane | 40 to 75 | 25 to 70 | 25 to 70 | 25 to 70 | 35 to 55 |
| ethanol | 10 to 60 | 15 to 50 | 15 to 50 | 20 to 40 | 20 to 40 |
| optional additives | to 100 | to 100 | to 100 | to 100 | to 100 |

* formed from the monomers i) N-tert-octylacrylamide, ii) acrylic acid, iii) tert.-butylaminoethyl methacrylate, iv) methyl methacrylate und v) hydroxypropyl methacrylate

|  | Formula 61 | Formula 62 | Formula 63 | Formula 64 | Formula 65 |
|---|---|---|---|---|---|
| copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| ethanol | 10 to 60 | 15 to 50 | 15 to 50 | 20 to 40 | 20 to 40 |
| water | <5.0 | <3.0 | <3.0 | <1.0 | <1.0 |
| optional additives | to 100 | to 100 | to 100 | to 100 | to 100 |

* formed from the monomers i) N-tert-octylacrylamide, ii) acrylic acid, iii) tert.-butylaminoethyl methacrylate and optionally further monomers

|  | Formula 66 | Formula 67 | Formula 68 | Formula 69 | Formula 70 |
|---|---|---|---|---|---|
| copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| ethanol | 10 to 60 | 15 to 50 | 15 to 50 | 20 to 40 | 20 to 40 |
| water | <5.0 | <3.0 | <3.0 | <1.0 | <1.0 |
| optional additives | to 100 | to 100 | to 100 | to 100 | to 100 |

* formed from the monomers i) N-tert-octylacrylamide, ii) acrylic acid, iii) tert.-butylaminoethyl methacrylate, iv) methyl methacrylate und v) hydroxypropyl methacrylate

|  | Formula 71 | Formula 72 | Formula 73 | Formula 74 | Formula 75 |
|---|---|---|---|---|---|
| copolymer * | 0.5 to 10 | 0.5 to 10 | 1.0 to 10 | 1.0 to 10 | 3.0 to 7.0 |
| cyclopenta-siloxane | 40 to 75 | 25 to 70 | 25 to 70 | 25 to 70 | 35 to 55 |
| ethanol | 10 to 60 | 15 to 50 | 15 to 50 | 20 to 40 | 20 to 40 |
| water | <5.0 | <3.0 | <3.0 | <1.0 | <1.0 |
| optional additives | to 100 | to 100 | to 100 | to 100 | to 100 |

* formed from the monomers i) N-tert-octylacrylamide, ii) acrylic acid, iii) tert.-butylaminoethyl methacrylate and optionally further monomers

|  | Formula 76 | Formula 77 | Formula 78 | Formula 79 | Formula 80 |
|---|---|---|---|---|---|
| copolymer * | 0.5 to 10 | 0.5 to 10 | 1.0 to 10 | 1.0 to 10 | 3.0 to 7.0 |
| cyclopenta-siloxane | 40 to 75 | 25 to 70 | 25 to 70 | 25 to 70 | 35 to 55 |
| ethanol | 10 to 60 | 15 to 50 | 15 to 50 | 20 to 40 | 20 to 40 |
| water | <5.0 | <3.0 | <3.0 | <1.0 | <1.0 |
| optional additives | to 100 | to 100 | to 100 | to 100 | to 100 |

* formed from the monomers i) N-tert-octylacrylamide, ii) acrylic acid, iii) tert.-butylaminoethyl methacrylate, iv) methyl methacrylate und v) hydroxypropyl methacrylate

|  | Formula 81 | Formula 82 | Formula 83 | Formula 84 | Formula 85 |
|---|---|---|---|---|---|
| copolymer * | 0.5 to 10 | 0.5 to 10 | 1.0 to 10 | 1.0 to 10 | 3.0 to 7.0 |
| cyclopenta-siloxane | 40 to 75 | 25 to 70 | 25 to 70 | 25 to 70 | 35 to 55 |
| ethanol | 10 to 60 | 15 to 50 | 15 to 50 | 20 to 40 | 20 to 40 |
| water | <5.0 | <3.0 | <3.0 | <1.0 | <1.0 |
| optional additives | to 100 | to 100 | to 100 | to 100 | to 100 |

* with the INCI name Octylacrylamide/Acrylates/Butylaminoethyl Methacrylate Copolymer Besides the above-described ingredients, the deodorizing cosmetic agents can also contain further active substances and auxiliaries. For example, enzyme inhibitors belong to the group of these further active substances and auxiliaries.

Suitable enzyme inhibitors are for example esterase inhibitors. These are preferably trialkyl citrates, such as trimethyl citrate, tripropyl citrate, triisopropyl citrate, tributyl citrate, and in particular triethyl citrate (Hydagen® CAT). The substances inhibit enzyme activity and thus reduce the development of odor. Further substances which can be considered as esterase inhibitors are sterol sulfates or phosphates, such as lanosterol, cholesterol, campesterol, stigmasterol and sitosterol sulfate or phosphate, dicarboxylic acids and esters thereof, such as glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, such as citric acid, malic acid, tartaric acid or tartaric acid diethyl ester, and zinc glycinate. Particularly suitable enzyme inhibitors are selected from the group of trialkyl citric acid esters, for example from triethyl citrate or zinc glycinate, in particular triethyl citrate.

Suitable agents contain, in relation to their total weight, from about 2.0 to about 20% by weight, for example from about 4.0 to about 16% by weight, and in particular from about 8.0 to about 12% by weight of enzyme inhibitor.

The composition of cosmetic agents that are more suitable can be inferred from the following tables (values in % by weight in relation to the total weight of the cosmetic agent unless specified otherwise).

|  | Formula 101 | Formula 102 | Formula 103 | Formula 104 | Formula 105 |
| --- | --- | --- | --- | --- | --- |
| copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| enzyme inhibitor ** | 2.0 to 20 | 2.0 to 20 | 4.0 to 16 | 4.0 to 16 | 8.0 to 12 |
| optional additives | to 100 | to 100 | to 100 | to 100 | to 100 |

* formed from the monomers i) N-tert-octylacrylamide, ii) acrylic acid, iii) tert.-butylaminoethyl methacrylate and optionally further monomers

|  | Formula 106 | Formula 107 | Formula 108 | Formula 109 | Formula 110 |
| --- | --- | --- | --- | --- | --- |
| Copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| enzyme inhibitor ** | 2.0 to 20 | 2.0 to 20 | 4.0 to 16 | 4.0 to 16 | 8.0 to 12 |
| optional additives | to 100 | to 100 | to 100 | to 100 | to 100 |

* formed from the monomers i) N-tert-octylacrylamide, ii) acrylic acid, iii) tert.-butylaminoethyl methacrylate, iv) methyl methacrylate und v) hydroxypropyl methacrylate

|  | Formula 111 | Formula 112 | Formula 113 | Formula 114 | Formula 115 |
| --- | --- | --- | --- | --- | --- |
| copolymer * cyclopentasiloxane | 0.5 to 10 40 to 75 | 0.5 to 10 25 to 70 | 1.0 to 10 25 to 70 | 1.0 to 10 25 to 70 | 3.0 to 7.0 35 to 55 |
| enzyme inhibitor ** | 2.0 to 20 | 2.0 to 20 | 4.0 to 16 | 4.0 to 16 | 8.0 to 12 |
| optional additives | to 100 | to 100 | to 100 | to 100 | to 100 |

* formed from the monomers i) N-tert-octylacrylamide, ii) acrylic acid, iii) tert.-butylaminoethyl methacrylate and optionally further monomers

|  | Formula 116 | Formula 117 | Formula 118 | Formula 119 | Formula 120 |
| --- | --- | --- | --- | --- | --- |
| copolymer * cyclopentasiloxane | 0.5 to 10 40 to 75 | 0.5 to 10 25 to 70 | 1.0 to 10 25 to 70 | 1.0 to 10 25 to 70 | 3.0 to 7.0 35 to 55 |
| enzyme inhibitor ** | 2.0 to 20 | 2.0 to 20 | 4.0 to 16 | 4.0 to 16 | 8.0 to 12 |
| optional additives | to 100 | to 100 | to 100 | to 100 | to 100 |

* formed from the monomers i) N-tert-octylacrylamide, ii) acrylic acid, iii) tert.-butylaminoethyl methacrylate, iv) methyl methacrylate und v) hydroxypropyl methacrylate

|  | Formula 121 | Formula 122 | Formula 123 | Formula 124 | Formula 125 |
| --- | --- | --- | --- | --- | --- |
| copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| enzyme inhibitor ** | 2.0 to 20 | 2.0 to 20 | 4.0 to 16 | 4.0 to 16 | 8.0 to 12 |
| hydrophilic organic solvent | 10 to 60 | 15 to 50 | 15 to 50 | 20 to 40 | 20 to 40 |
| optional additives | to 100 | to 100 | to 100 | to 100 | to 100 |

* formed from the monomers i) N-tert-octylacrylamide, ii) acrylic acid, iii) tert.-butylaminoethyl methacrylate and optionally further monomers

|  | Formula 126 | Formula 127 | Formula 128 | Formula 129 | Formula 130 |
| --- | --- | --- | --- | --- | --- |
| copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| enzyme inhibitor ** | 2.0 to 20 | 2.0 to 20 | 4.0 to 16 | 4.0 to 16 | 8.0 to 12 |
| hydrophilic organic solvent | 10 to 60 | 15 to 50 | 15 to 50 | 20 to 40 | 20 to 40 |
| optional additives | to 100 | to 100 | to 100 | to 100 | to 100 |

* formed from the monomers i) N-tert-octylacrylamide, ii) acrylic acid, iii) tert.-butylaminoethyl methacrylate, iv) methyl methacrylate und v) hydroxypropyl methacrylate

|  | Formula 131 | Formula 132 | Formula 133 | Formula 134 | Formula 135 |
| --- | --- | --- | --- | --- | --- |
| copolymer * cyclopentasiloxane | 0.5 to 10 40 to 75 | 0.5 to 10 25 to 70 | 1.0 to 10 25 to 70 | 1.0 to 10 25 to 70 | 3.0 to 7.0 35 to 55 |
| enzyme inhibitor ** | 2.0 to 20 | 2.0 to 20 | 4.0 to 16 | 4.0 to 16 | 8.0 to 12 |
| hydrophilic organic solvent | 10 to 60 | 15 to 50 | 15 to 50 | 20 to 40 | 20 to 40 |

-continued

|  | Formula 131 | Formula 132 | Formula 133 | Formula 134 | Formula 135 |
|---|---|---|---|---|---|
| optional additives | to 100 | to 100 | to 100 | to 100 | to 100 |

* formed from the monomers i) N-tert-octylacrylamide, ii) acrylic acid, iii) tert.-butylaminoethyl methacrylate and optionally further monomers

|  | Formula 136 | Formula 137 | Formula 138 | Formula 139 | Formula 140 |
|---|---|---|---|---|---|
| copolymer * | 0.5 to 10 | 0.5 to 10 | 1.0 to 10 | 1.0 to 10 | 3.0 to 7.0 |
| cyclopentasiloxane | 40 to 75 | 25 to 70 | 25 to 70 | 25 to 70 | 35 to 55 |
| enzyme inhibitor ** | 2.0 to 20 | 2.0 to 20 | 4.0 to 16 | 4.0 to 16 | 8.0 to 12 |
| hydrophilic organic solvent | 10 to 60 | 15 to 50 | 15 to 50 | 20 to 40 | 20 to 40 |
| optional additives | to 100 | to 100 | to 100 | to 100 | to 100 |

* formed from the monomers i) N-tert-octylacrylamide, ii) acrylic acid, iii) tert.-butylaminoethyl methacrylate, iv) methyl methacrylate und v) hydroxypropyl methacrylate

|  | Formula 141 | Formula 142 | Formula 143 | Formula 144 | Formula 145 |
|---|---|---|---|---|---|
| copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| enzyme inhibitor ** | 2.0 to 20 | 2.0 to 20 | 4.0 to 16 | 4.0 to 16 | 8.0 to 12 |
| ethanol | 10 to 60 | 15 to 50 | 15 to 50 | 20 to 40 | 20 to 40 |
| optional additives | to 100 | to 100 | to 100 | to 100 | to 100 |

* formed from the monomers i) N-tert-octylacrylamide, ii) acrylic acid, iii) tert.-butylaminoethyl methacrylate and optionally further monomers

|  | Formula 146 | Formula 147 | Formula 148 | Formula 149 | Formula 150 |
|---|---|---|---|---|---|
| copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| enzyme inhibitor ** | 2.0 to 20 | 2.0 to 20 | 4.0 to 16 | 4.0 to 16 | 8.0 to 12 |
| ethanol | 10 to 60 | 15 to 50 | 15 to 50 | 20 to 40 | 20 to 40 |
| optional additives | to 100 | to 100 | to 100 | to 100 | to 100 |

* formed from the monomers i) N-tert-octylacrylamide, ii) acrylic acid, iii) tert.-butylaminoethyl methacrylate, iv) methyl methacrylate und v) hydroxypropyl methacrylate

|  | Formula 151 | Formula 152 | Formula 153 | Formula 154 | Formula 155 |
|---|---|---|---|---|---|
| copolymer * | 0.5 to 10 | 0.5 to 10 | 1.0 to 10 | 1.0 to 10 | 3.0 to 7.0 |
| cyclopentasiloxane | 40 to 75 | 25 to 70 | 25 to 70 | 25 to 70 | 35 to 55 |
| enzyme inhibitor ** | 2.0 to 20 | 2.0 to 20 | 4.0 to 16 | 4.0 to 16 | 8.0 to 12 |
| ethanol | 10 to 60 | 15 to 50 | 15 to 50 | 20 to 40 | 20 to 40 |
| optional additives | to 100 | to 100 | to 100 | to 100 | to 100 |

* formed from the monomers i) N-tert-octylacrylamide, ii) acrylic acid, iii) tert.-butylaminoethyl methacrylate and optionally further monomers

|  | Formula 156 | Formula 157 | Formula 158 | Formula 159 | Formula 160 |
|---|---|---|---|---|---|
| copolymer * | 0.5 to 10 | 0.5 to 10 | 1.0 to 10 | 1.0 to 10 | 3.0 to 7.0 |
| cyclopentasiloxane | 40 to 75 | 25 to 70 | 25 to 70 | 25 to 70 | 35 to 55 |
| enzyme inhibitor ** | 2.0 to 20 | 2.0 to 20 | 4.0 to 16 | 4.0 to 16 | 8.0 to 12 |
| ethanol | 10 to 60 | 15 to 50 | 15 to 50 | 20 to 40 | 20 to 40 |
| optional additives | to 100 | to 100 | to 100 | to 100 | to 100 |

* formed from the monomers i) N-tert-octylacrylamide, ii) acrylic acid, iii) tert.-butylaminoethyl methacrylate, iv) methyl methacrylate und v) hydroxypropyl methacrylate

|  | Formula 161 | Formula 162 | Formula 163 | Formula 164 | Formula 165 |
|---|---|---|---|---|---|
| copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| enzyme inhibitor ** | 2.0 to 20 | 2.0 to 20 | 4.0 to 16 | 4.0 to 16 | 8.0 to 12 |
| ethanol | 10 to 60 | 15 to 50 | 15 to 50 | 20 to 40 | 20 to 40 |
| water | <5.0 | <3.0 | <3.0 | <1.0 | <1.0 |
| optional additives | to 100 | to 100 | to 100 | to 100 | to 100 |

* formed from the monomers i) N-tert-octylacrylamide, ii) acrylic acid, iii) tert.-butylaminoethyl methacrylate and optionally further monomers

|  | Formula 166 | Formula 167 | Formula 168 | Formula 169 | Formula 170 |
|---|---|---|---|---|---|
| copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| enzyme inhibitor ** | 2.0 to 20 | 2.0 to 20 | 4.0 to 16 | 4.0 to 16 | 8.0 to 12 |
| ethanol | 10 to 60 | 15 to 50 | 15 to 50 | 20 to 40 | 20 to 40 |
| water | <5.0 | <3.0 | <3.0 | <1.0 | <1.0 |
| optional additives | to 100 | to 100 | to 100 | to 100 | to 100 |

* formed from the monomers i) N-tert-octylacrylamide, ii) acrylic acid, iii) tert.-butylaminoethyl methacrylate, iv) methyl methacrylate und v) hydroxypropyl methacrylate

|  | Formula 171 | Formula 172 | Formula 173 | Formula 174 | Formula 175 |
|---|---|---|---|---|---|
| copolymer * | 0.5 to 10 | 0.5 to 10 | 1.0 to 10 | 1.0 to 10 | 3.0 to 7.0 |
| cyclopentasiloxane | 40 to 75 | 25 to 70 | 25 to 70 | 25 to 70 | 35 to 55 |
| enzyme inhibitor ** | 2.0 to 20 | 2.0 to 20 | 4.0 to 16 | 4.0 to 16 | 8.0 to 12 |
| ethanol | 10 to 60 | 15 to 50 | 15 to 50 | 20 to 40 | 20 to 40 |
| water | <5.0 | <3.0 | <3.0 | <1.0 | <1.0 |
| optional additives | to 100 | to 100 | to 100 | to 100 | to 100 |

* formed from the monomers i) N-tert-octylacrylamide, ii) acrylic acid, iii) tert.-butylaminoethyl methacrylate and optionally further monomers

|  | Formula 176 | Formula 177 | Formula 178 | Formula 179 | Formula 180 |
|---|---|---|---|---|---|
| copolymer * | 0.5 to 10 | 0.5 to 10 | 1.0 to 10 | 1.0 to 10 | 3.0 to 7.0 |
| cyclopentasiloxane | 40 to 75 | 25 to 70 | 25 to 70 | 25 to 70 | 35 to 55 |
| enzyme inhibitor ** | 2.0 to 20 | 2.0 to 20 | 4.0 to 16 | 4.0 to 16 | 8.0 to 12 |

-continued

|  | Formula 176 | Formula 177 | Formula 178 | Formula 179 | Formula 180 |
|---|---|---|---|---|---|
| ethanol | 10 to 60 | 15 to 50 | 15 to 50 | 20 to 40 | 20 to 40 |
| water | <5.0 | <3.0 | <3.0 | <1.0 | <1.0 |
| optional additives | to 100 | to 100 | to 100 | to 100 | to 100 |

* formed from the monomers i) N-tert-octylacrylamide, ii) acrylic acid, iii) tert.-butylaminoethyl methacrylate, iv) methyl methacrylate und v) hydroxypropyl methacrylate
** preferably triethyl citrate

|  | Formula 181 | Formula 182 | Formula 183 | Formula 184 | Formula 185 |
|---|---|---|---|---|---|
| copolymer * | 0.5 to 10 | 0.5 to 10 | 1.0 to 10 | 1.0 to 10 | 3.0 to 7.0 |
| cyclopenta-siloxane | 40 to 75 | 25 to 70 | 25 to 70 | 25 to 70 | 35 to 55 |
| enzyme inhibitor ** | 2.0 to 20 | 2.0 to 20 | 4.0 to 16 | 4.0 to 16 | 8.0 to 12 |
| ethanol | 10 to 60 | 15 to 50 | 15 to 50 | 20 to 40 | 20 to 40 |
| water | <5.0 | <3.0 | <3.0 | <1.0 | <1.0 |
| optional additives | to 100 | to 100 | to 100 | to 100 | to 100 |

* with the INCI name Octylacrylamide/Acrylates/Butylaminoethyl Methacrylate Copolymer
** preferably triethyl citrate A further group of optional active substances and auxiliaries is constituted by thickeners, which are used to adjust viscosity. The thickener is different from the copolymer and oil constituents contained mandatorily in the cosmetic agents. A particularly suitable thickener is constituted by the hydrophobically modified silicates, in particular the hydrophobised hectorites, particularly preferably the hydrophobised hectorites with the INCI name Quaternium-18 Hectorite, as are sold for example under the trade name Bentone 38 (Elementis).

Suitable cosmetic agents contain the thickener, in particular the hydrophobically modified silicates, particularly preferably the hydrophobised hectorite in amounts of from in amounts of from about 0.5 to about 10% by weight, preferably of from about 1.0 to about 9.0% by weight, and in particular von from about 4.0 to about 8.0% by weight, in each case in relation to the total weight of the cosmetic agent.

The composition of further suitable cosmetic agents is presented in the following tables (values in % by weight in relation to the total weight of the cosmetic agent unless specified otherwise).

|  | Formula 201 | Formula 202 | Formula 203 | Formula 204 | Formula 205 |
|---|---|---|---|---|---|
| copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| thickener ** | 0.5 to 10 | 1.0 to 9.0 | 1.0 to 9.0 | 1.0 to 9.0 | 4.0 to 8.0 |
| optional additives | to 100 | to 100 | to 100 | to 100 | to 100 |

* formed from the monomers i) N-tert-octylacrylamide, ii) acrylic acid, iii) tert.-butylaminoethyl methacrylate and optionally further monomers
** preferably hydrophobised hectorite, in particular hydrophobised hectorite with the INCI name Quaternium-18 Hectorite

|  | Formula 206 | Formula 207 | Formula 208 | Formula 209 | Formula 210 |
|---|---|---|---|---|---|
| copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| thickener ** | 0.5 to 10 | 1.0 to 9.0 | 1.0 to 9.0 | 1.0 to 9.0 | 4.0 to 8.0 |
| optional additives | to 100 | to 100 | to 100 | to 100 | to 100 |

* formed from the monomers i) N-tert-octylacrylamide, ii) acrylic acid, iii) tert.-butylaminoethyl methacrylate, iv) methyl methacrylate und v) hydroxypropyl methacrylate
** preferably hydrophobised hectorite, in particular hydrophobised hectorite with the INCI name Quaternium-18 Hectorite

|  | Formula 211 | Formula 212 | Formula 213 | Formula 214 | Formula 215 |
|---|---|---|---|---|---|
| copolymer * | 0.5 to 10 | 0.5 to 10 | 1.0 to 10 | 1.0 to 10 | 3.0 to 7.0 |
| cyclopenta-siloxane | 40 to 75 | 25 to 70 | 25 to 70 | 25 to 70 | 35 to 55 |
| thickener ** | 0.5 to 10 | 1.0 to 9.0 | 1.0 to 9.0 | 1.0 to 9.0 | 4.0 to 8.0 |
| optional additives | to 100 | to 100 | to 100 | to 100 | to 100 |

* formed from the monomers i) N-tert-octylacrylamide, ii) acrylic acid, iii) tert.-butylaminoethyl methacrylate and optionally further monomers
** preferably hydrophobised hectorite, in particular hydrophobised hectorite with the INCI name Quaternium-18 Hectorite

|  | Formula 216 | Formula 217 | Formula 218 | Formula 219 | Formula 220 |
|---|---|---|---|---|---|
| copolymer * | 0.5 to 10 | 0.5 to 10 | 1.0 to 10 | 1.0 to 10 | 3.0 to 7.0 |
| cyclopenta-siloxane | 40 to 75 | 25 to 70 | 25 to 70 | 25 to 70 | 35 to 55 |
| thickener ** | 0.5 to 10 | 1.0 to 9.0 | 1.0 to 9.0 | 1.0 to 9.0 | 4.0 to 8.0 |
| optional additives | to 100 | to 100 | to 100 | to 100 | to 100 |

* formed from the monomers i) N-tert-octylacrylamide, ii) acrylic acid, iii) tert.-butylaminoethyl methacrylate, iv) methyl methacrylate und v) hydroxypropyl methacrylate
** preferably hydrophobised hectorite, in particular hydrophobised hectorite with the INCI name Quaternium-18 Hectorite

|  | Formula 221 | Formula 222 | Formula 223 | Formula 224 | Formula 225 |
|---|---|---|---|---|---|
| Copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| thickener ** | 0.5 to 10 | 1.0 to 9.0 | 1.0 to 9.0 | 1.0 to 9.0 | 4.0 to 8.0 |
| hydrophilic organic solvent | 10 to 60 | 15 to 50 | 15 to 50 | 20 to 40 | 20 to 40 |
| optional additives | to 100 | to 100 | to 100 | to 100 | to 100 |

* formed from the monomers i) N-tert-octylacrylamide, ii) acrylic acid, iii) tert.-butylaminoethyl methacrylate and optionally further monomers
** preferably hydrophobised hectorite, in particular hydrophobised hectorite with the INCI name Quaternium-18 Hectorite

|  | Formula 226 | Formula 227 | Formula 228 | Formula 229 | Formula 230 |
|---|---|---|---|---|---|
| Copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| thickener ** | 0.5 to 10 | 1.0 to 9.0 | 1.0 to 9.0 | 1.0 to 9.0 | 4.0 to 8.0 |
| hydrophilic organic solvent | 10 to 60 | 15 to 50 | 15 to 50 | 20 to 40 | 20 to 40 |

-continued

|  | Formula 226 | Formula 227 | Formula 228 | Formula 229 | Formula 230 |
|---|---|---|---|---|---|
| optional additives | to 100 | to 100 | to 100 | to 100 | to 100 |

\* formed from the monomers i) N-tert-octylacrylamide, ii) acrylic acid, iii) tert.-butylaminoethyl methacrylate, iv) methyl methacrylate und v) hydroxypropyl methacrylate
\*\* preferably hydrophobised hectorite, in particular hydrophobised hectorite with the INCI name Quaternium-18 Hectorite

|  | Formula 231 | Formula 232 | Formula 233 | Formula 234 | Formula 235 |
|---|---|---|---|---|---|
| copolymer \* | 0.5 to 10 | 0.5 to 10 | 1.0 to 10 | 1.0 to 10 | 3.0 to 7.0 |
| cyclopentasiloxane | 40 to 75 | 25 to 70 | 25 to 70 | 25 to 70 | 35 to 55 |
| thickener \*\* | 0.5 to 10 | 1.0 to 9.0 | 1.0 to 9.0 | 1.0 to 9.0 | 4.0 to 8.0 |
| hydrophilic organic solvent | 10 to 60 | 15 to 50 | 15 to 50 | 20 to 40 | 20 to 40 |
| optional additives | to 100 | to 100 | to 100 | to 100 | to 100 |

\* formed from the monomers i) N-tert-octylacrylamide, ii) acrylic acid, iii) tert.-butylaminoethyl methacrylate and optionally further monomers
\*\* preferably hydrophobised hectorite, in particular hydrophobised hectorite with the INCI name Quaternium-18 Hectorite

|  | Formula 236 | Formula 237 | Formula 238 | Formula 239 | Formula 240 |
|---|---|---|---|---|---|
| copolymer \* | 0.5 to 10 | 0.5 to 10 | 1.0 to 10 | 1.0 to 10 | 3.0 to 7.0 |
| cyclopentasiloxane | 40 to 75 | 25 to 70 | 25 to 70 | 25 to 70 | 35 to 55 |
| thickener \*\* | 0.5 to 10 | 1.0 to 9.0 | 1.0 to 9.0 | 1.0 to 9.0 | 4.0 to 8.0 |
| hydrophilic organic solvent | 10 to 60 | 15 to 50 | 15 to 50 | 20 to 40 | 20 to 40 |
| optional additives | to 100 | to 100 | to 100 | to 100 | to 100 |

\* formed from the monomers i) N-tert-octylacrylamide, ii) acrylic acid, iii) tert.-butylaminoethyl methacrylate, iv) methyl methacrylate und v) hydroxypropyl methacrylate
\*\* preferably hydrophobised hectorite, in particular hydrophobised hectorite with the INCI name Quaternium-18 Hectorite

|  | Formula 241 | Formula 242 | Formula 243 | Formula 244 | Formula 245 |
|---|---|---|---|---|---|
| copolymer \* | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| thickener \*\* | 0.5 to 10 | 1.0 to 9.0 | 1.0 to 9.0 | 1.0 to 9.0 | 4.0 to 8.0 |
| ethanol | 10 to 60 | 15 to 50 | 15 to 50 | 20 to 40 | 20 to 40 |
| optional additives | to 100 | to 100 | to 100 | to 100 | to 100 |

\* formed from the monomers i) N-tert-octylacrylamide, ii) acrylic acid, iii) tert.-butylaminoethyl methacrylate and optionally further monomers
\*\* preferably hydrophobised hectorite, in particular hydrophobised hectorite with the INCI name Quaternium-18 Hectorite

|  | Formula 246 | Formula 247 | Formula 248 | Formula 249 | Formula 250 |
|---|---|---|---|---|---|
| copolymer \* | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| thickener \*\* | 0.5 to 10 | 1.0 to 9.0 | 1.0 to 9.0 | 1.0 to 9.0 | 4.0 to 8.0 |
| ethanol | 10 to 60 | 15 to 50 | 15 to 50 | 20 to 40 | 20 to 40 |
| optional additives | to 100 | to 100 | to 100 | to 100 | to 100 |

\* formed from the monomers i) N-tert-octylacrylamide, ii) acrylic acid, iii) tert.-butylaminoethyl methacrylate, iv) methyl methacrylate und v) hydroxypropyl methacrylate
\*\* preferably hydrophobised hectorite, in particular hydrophobised hectorite with the INCI name Quaternium-18 Hectorite

|  | Formula 251 | Formula 252 | Formula 253 | Formula 254 | Formula 255 |
|---|---|---|---|---|---|
| copolymer \* | 0.5 to 10 | 0.5 to 10 | 1.0 to 10 | 1.0 to 10 | 3.0 to 7.0 |
| cyclopentasiloxane | 40 to 75 | 25 to 70 | 25 to 70 | 25 to 70 | 35 to 55 |
| thickener \*\* | 0.5 to 10 | 1.0 to 9.0 | 1.0 to 9.0 | 1.0 to 9.0 | 4.0 to 8.0 |
| ethanol | 10 to 60 | 15 to 50 | 15 to 50 | 20 to 40 | 20 to 40 |
| optional additives | to 100 | to 100 | to 100 | to 100 | to 100 |

\* formed from the monomers i) N-tert-octylacrylamide, ii) acrylic acid, iii) tert.-butylaminoethyl methacrylate and optionally further monomers
\*\* preferably hydrophobised hectorite, in particular hydrophobised hectorite with the INCI name Quaternium-18 Hectorite

|  | Formula 256 | Formula 257 | Formula 258 | Formula 259 | Formula 260 |
|---|---|---|---|---|---|
| copolymer \* | 0.5 to 10 | 0.5 to 10 | 1.0 to 10 | 1.0 to 10 | 3.0 to 7.0 |
| cyclopentasiloxane | 40 to 75 | 25 to 70 | 25 to 70 | 25 to 70 | 35 to 55 |
| thickener \*\* | 0.5 to 10 | 1.0 to 9.0 | 1.0 to 9.0 | 1.0 to 9.0 | 4.0 to 8.0 |
| ethanol | 10 to 60 | 15 to 50 | 15 to 50 | 20 to 40 | 20 to 40 |
| optional additives | to 100 | to 100 | to 100 | to 100 | to 100 |

\* formed from the monomers i) N-tert-octylacrylamide, ii) acrylic acid, iii) tert.-butylaminoethyl methacrylate, iv) methyl methacrylate und v) hydroxypropyl methacrylate
\*\* preferably hydrophobised hectorite, in particular hydrophobised hectorite with the INCI name Quaternium-18 Hectorite

|  | Formula 261 | Formula 262 | Formula 263 | Formula 264 | Formula 265 |
|---|---|---|---|---|---|
| copolymer \* | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| thickener \*\* | 0.5 to 10 | 1.0 to 9.0 | 1.0 to 9.0 | 1.0 to 9.0 | 4.0 to 8.0 |
| ethanol | 10 to 60 | 15 to 50 | 15 to 50 | 20 to 40 | 20 to 40 |
| water | <5.0 | <3.0 | <3.0 | <1.0 | <1.0 |
| optional additives | to 100 | to 100 | to 100 | to 100 | to 100 |

\* formed from the monomers i) N-tert-octylacrylamide, ii) acrylic acid, iii) tert.-butylaminoethyl methacrylate and optionally further monomers
\*\* preferably hydrophobised hectorite, in particular hydrophobised hectorite with the INCI name Quaternium-18 Hectorite

|  | Formula 266 | Formula 267 | Formula 268 | Formula 269 | Formula 270 |
|---|---|---|---|---|---|
| copolymer \* | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| thickener \*\* | 0.5 to 10 | 1.0 to 9.0 | 1.0 to 9.0 | 1.0 to 9.0 | 4.0 to 8.0 |
| ethanol | 10 to 60 | 15 to 50 | 15 to 50 | 20 to 40 | 20 to 40 |
| water | <5.0 | <3.0 | <3.0 | <1.0 | <1.0 |

-continued

|  | Formula 266 | Formula 267 | Formula 268 | Formula 269 | Formula 270 |
|---|---|---|---|---|---|
| optional additives | to 100 | to 100 | to 100 | to 100 | to 100 |

\* formed from the monomers i) N-tert-octylacrylamide, ii) acrylic acid, iii) tert.-butylaminoethyl methacrylate, iv) methyl methacrylate und v) hydroxypropyl methacrylate
\*\* preferably hydrophobised hectorite, in particular hydrophobised hectorite with the INCI name Quaternium-18 Hectorite

|  | Formula 271 | Formula 272 | Formula 273 | Formula 274 | Formula 275 |
|---|---|---|---|---|---|
| copolymer * | 0.5 to 10 | 0.5 to 10 | 1.0 to 10 | 1.0 to 10 | 3.0 to 7.0 |
| cyclopenta-siloxane | 40 to 75 | 25 to 70 | 25 to 70 | 25 to 70 | 35 to 55 |
| thickener ** | 0.5 to 10 | 1.0 to 9.0 | 1.0 to 9.0 | 1.0 to 9.0 | 4.0 to 8.0 |
| ethanol | 10 to 60 | 15 to 50 | 15 to 50 | 20 to 40 | 20 to 40 |
| water | <5.0 | <3.0 | <3.0 | <1.0 | <1.0 |
| optional additives | to 100 | to 100 | to 100 | to 100 | to 100 |

\* formed from the monomers i) N-tert-octylacrylamide, ii) acrylic acid, iii) tert.-butylaminoethyl methacrylate and optionally further monomers
\*\* preferably hydrophobised hectorite, in particular hydrophobised hectorite with the INCI name Quaternium-18 Hectorite

|  | Formula 276 | Formula 277 | Formula 278 | Formula 279 | Formula 280 |
|---|---|---|---|---|---|
| copolymer * | 0.5 to 10 | 0.5 to 10 | 1.0 to 10 | 1.0 to 10 | 3.0 to 7.0 |
| cyclopenta-siloxane | 40 to 75 | 25 to 70 | 25 to 70 | 25 to 70 | 35 to 55 |
| thickener ** | 0.5 to 10 | 1.0 to 9.0 | 1.0 to 9.0 | 1.0 to 9.0 | 4.0 to 8.0 |
| ethanol | 10 to 60 | 15 to 50 | 15 to 50 | 20 to 40 | 20 to 40 |
| water | <5.0 | <3.0 | <3.0 | <1.0 | <1.0 |
| optional additives | to 100 | to 100 | to 100 | to 100 | to 100 |

\* formed from the monomers i) N-tert-octylacrylamide, ii) acrylic acid, iii) tert.-butylaminoethyl methacrylate, iv) methyl methacrylate und v) hydroxypropyl methacrylate
\*\* preferably hydrophobised hectorite, in particular hydrophobised hectorite with the INCI name Quaternium-18 Hectorite

|  | Formula 281 | Formula 282 | Formula 283 | Formula 284 | Formula 285 |
|---|---|---|---|---|---|
| copolymer * | 0.5 to 10 | 0.5 to 10 | 1.0 to 10 | 1.0 to 10 | 3.0 to 7.0 |
| cyclopenta-siloxane | 40 to 75 | 25 to 70 | 25 to 70 | 25 to 70 | 35 to 55 |
| thickener ** | 0.5 to 10 | 1.0 to 9.0 | 1.0 to 9.0 | 1.0 to 9.0 | 4.0 to 8.0 |
| ethanol | 10 to 60 | 15 to 50 | 15 to 50 | 20 to 40 | 20 to 40 |
| water | <5.0 | <3.0 | <3.0 | <1.0 | <1.0 |
| optional additives | to 100 | to 100 | to 100 | to 100 | to 100 |

\* with the INCI name Octylacrylamide/Acrylates/Butylaminoethyl Methacrylate Copolymer
\*\* preferably hydrophobised hectorite, in particular hydrophobised hectorite with the INCI name Quaternium-18 Hectorite Cosmetic agents which consist largely of copolymer, oil, hydrophilic organic solvent, enzyme inhibitor and thickener have proven to be very effective. For reasons of cosmetic efficacy and with the objective of minimising the complexity of the production of these agents, it is therefore suitable that the deodorizing cosmetic agent, in relation to its total weight, of at least about 80% by weight, for example at least about 90% by weight, and in particular at least about 95% by weight
  a) of at least one copolymer formed from the monomers
    i) N-tert-octylacrylamide
    ii) acrylic acid
    iii) tert.-butylaminoethyl methacrylate
    iv) and optionally further monomers
  b) oil that is liquid at about 20° C. and about 1.013 hPa
  c) hydrophilic organic solvent
  d) enzyme inhibitor
  e) thickener.

The composition of cosmetic agents that are very particularly suitable can be inferred from the following tables (values in % by weight in relation to the total weight of the cosmetic agent unless specified otherwise).

|  | Formula 401 | Formula 402 | Formula 403 | Formula 404 | Formula 405 |
|---|---|---|---|---|---|
| copolymer * | 0.5 to 10 | 0.5 to 10 | 1.0 to 10 | 1.0 to 10 | 3.0 to 7.0 |
| liquid oil (20° C., 1.013 hPa) | 40 to 75 | 25 to 70 | 25 to 70 | 25 to 70 | 35 to 55 |
| enzyme inhibitor | 2.0 to 20 | 2.0 to 20 | 4.0 to 16 | 4.0 to 16 | 8.0 to 12 |
| thickener | 0.5 to 10 | 1.0 to 9.0 | 1.0 to 9.0 | 1.0 to 9.0 | 4.0 to 8.0 |
| ethanol | 10 to 60 | 15 to 50 | 15 to 50 | 20 to 40 | 20 to 40 |
| water | <5.0 | <3.0 | <3.0 | <1.0 | <1.0 |
| optional additives | to 100 | to 100 | to 100 | to 100 | to 100 |

\* formed from the monomers i) N-tert-octylacrylamide, ii) acrylic acid, iii) tert.-butylaminoethyl methacrylate and optionally further monomers

|  | Formula 401 | Formula 402 | Formula 403 | Formula 404 | Formula 405 |
|---|---|---|---|---|---|
| copolymer * | 0.5 to 10 | 0.5 to 10 | 1.0 to 10 | 1.0 to 10 | 3.0 to 7.0 |
| cyclopenta-siloxane | 40 to 75 | 25 to 70 | 25 to 70 | 25 to 70 | 35 to 55 |
| triethyl citrate | 2.0 to 20 | 2.0 to 20 | 4.0 to 16 | 4.0 to 16 | 8.0 to 12 |
| hydrophobised hectorite ** | 0.5 to 10 | 1.0 to 9.0 | 1.0 to 9.0 | 1.0 to 9.0 | 4.0 to 8.0 |
| ethanol | 10 to 60 | 15 to 50 | 15 to 50 | 20 to 40 | 20 to 40 |
| water | <5.0 | <3.0 | <3.0 | <1.0 | <1.0 |
| optional additives | to 100 | to 100 | to 100 | to 100 | to 100 |

\* with the INCI name Octylacrylamide/Acrylates/Butylaminoethyl Methacrylate Copolymer
\*\* with the INCI name Quaternium-18 Hectorite The deodorizing cosmetic agent can be applied by employing various methods. In accordance with a suitable embodiment the sweat-inhibiting cosmetic agent is formulated for spray-on application. The spray-on application is implemented using a spraying device, which contains a filling formed of the deodorizing cosmetic agent in a container. The filling can be performed under the pressure of a propellant (pressurised gas cans, pressurised gas packagings, aerosol packagings), or it can involve a pump atomiser that is to be operated mechanically, without propellant (pump spray/squeeze bottle). The use of a propellant, however, is suitable. Suitable cosmetic preparations therefore include, in addition to the cosmetic agent i), also at least one propellant ii).

Suitable propellants (propellant gases) are propane, propene, n-butane, iso-butane, iso-butene, n-pentane, pentene, iso-pentane, iso-pentene, methane, ethane, dimethyl ether, nitrogen, air, oxygen, nitrous oxide, 1,1,1,3-tetrafluoroethane, heptafluoro-n-propane, perfluoroethane, monochlorodifluoromethane, 1,1-difluoroethane, more specifically both individually and in combination. Hydrophilic propellant gas, such as carbon dioxide, can be used advantageously in the sense of the present disclosure if the proportion of hydrophilic gases is selected to be low and lipophilic propellant gas (for example propane/butane) is present in excess. Particularly suitable are propane, n-butane, iso-butane, and mixtures of these propellant gases. Suitable cosmetic agents are exemplified in that the agent is combined with at least one propellant b) from the group of mixtures of propane and butane and dimethyl ether.

Suitable cosmetic preparations include, in relation to their total weight
  i) from about 10 to about 30% by weight of cosmetic agent according to any one of the preceding points
  ii) from about 70 to about 90% by weight of propellant.

Vessels made of metal (aluminium, tinplate, tin), protected plastic or non-splintering plastic, or glass coated externally with plastic are potential pressurised gas containers for aerosol applications, wherein the compressive strength, breaking strength, corrosion resistance, ease of filling and also aesthetic considerations, ease of handling, printability, etc. play a role when selecting such a vessel. Special internal protective coatings ensure resistance to corrosion in respect of the cosmetic agent a).

If the agents as contemplated herein are to be sprayed, these agents are advantageously provided with a dispensing device and a spray valve. The resultant cosmetic products include accordingly a cosmetic agent as contemplated herein or a cosmetic preparation as contemplated herein, and also a dispensing device having a spray valve.

A further subject of the claims is a non-therapeutic cosmetic method for preventing and/or reducing body odor, in which a cosmetic agent as contemplated herein is applied to the skin, in particular the skin of the armpits, and is left on the skin for at least about 1 hour, preferably for at least about 2 hours, preferably for at least about 4 hours, and in particular for at least about 6 hours.

As mentioned at the outset, the cosmetic agents have an advantageous influence on the formation of body odor. The use of this cosmetic agent for preventing and/or reducing body odor is a further subject of the present application.

EXAMPLES

The following sprayable antiperspirant suspensions were produced (values in % by weight):

| | 1 | 2 | 3 |
|---|---|---|---|
| cyclopentasiloxane | to 100 | to 100 | to 100 |
| citric acid triethyl ester | 10.0 | 10.0 | 10.0 |
| ethanol | 20.5 | 20.5 | 35.0 |
| amphomer [1] | 1.5 | 1.0 | 5.0 |
| bentone 38 V CG [2] | 6.0 | 6.0 | 6.0 |
| propylene carbonate | 2.0 | 2.0 | 2.0 |
| sodium hydroxide | 0.005 | 0.005 | 0.005 |

[1] INCI name: Octylacrylamide/Acrylates/Butylaminoethyl Methacrylate Copolymer
[2] INCI name Quaternium-18 Hectorite The formulations were filled into aerosol cans together with the propellant propane/butane (15/85) in a weight ratio of 1:4.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An antiperspirant cosmetic agent comprising:
   a) from about 0.5 to about 10% by weight of at least one copolymer formed from at least the monomers:
      i) N-tert-octylacrylamide,
      ii) acrylic acid, and
      iii) tert.-butylaminoethyl methacrylate; and
   b) from about 25 to about 70% by weight of an oil that is in liquid state at about 20° C. and about 1.013 hPa,
      wherein the antiperspirant cosmetic agent does not contain any aluminium-containing compounds, and
      wherein the oil comprises cyclopentasiloxane.

2. The antiperspirant cosmetic agent according to claim 1, wherein the agent comprises, as copolymer a), at least one copolymer formed from at least the monomers:
   i) N-tert-octylacrylamide,
   ii) acrylic acid,
   iii) tert.-butylaminoethyl methacrylate,
   iv) methyl methacrylate, and
   v) hydroxypropyl methacrylate.

3. The antiperspirant cosmetic agent according to claim 1, wherein the copolymer a), in relation to the total weight of the agent, is included in an amount of from about 1.0 to about 10% by weight.

4. The antiperspirant cosmetic agent according to claim 1, wherein the oil, in relation to the total weight of the agent, is included in an amount of from about 35 to about 55% by weight.

5. The antiperspirant cosmetic agent according to claim 1 further comprising a hydrophilic organic solvent.

6. A cosmetic preparation comprising:
   i) the antiperspirant cosmetic agent according to claim 1; and
   ii) a propellant.

7. A cosmetic product comprising:
   i) the cosmetic preparation according to claim 6; and
   ii) a dispensing device having a spray valve.

8. A non-therapeutic cosmetic method for preventing and/or reducing body odor, the method comprising the steps of applying an antiperspirant cosmetic agent to a user's skin and leaving the antiperspirant cosmetic agent on the skin for at least about 1 hour, wherein the antiperspirant cosmetic agent comprises:
   a) from about 0.5 to about 10% by weight of at least one copolymer formed from at least the monomers:
      i) N-tert-octylacrylamide,
      ii) acrylic acid, and
      iii) tert.-butylaminoethyl methacrylate; and
   b) from about 25 to about 70% by weight of an oil that is in liquid state at about 20° C. and about 1.013 hPa,
      wherein the antiperspirant cosmetic agent does not contain any aluminium-containing compounds, and
      wherein the oil comprises cyclopentasiloxane.

9. The antiperspirant cosmetic agent according to claim 1, wherein the copolymer a), in relation to the total weight of the agent, is included in an amount of from about 3.0 to about 7.0% by weight.

10. The antiperspirant cosmetic agent according to claim 5, wherein the hydrophilic organic solvent, in relation to the total weight of the agent, is included in an amount of from about 10 to about 60% by weight.

11. The antiperspirant cosmetic agent according to claim 5, wherein the hydrophilic organic solvent, in relation to the total weight of the agent, is included in an amount of from about 15 to about 50% by weight.

12. The antiperspirant cosmetic agent according to claim 5, wherein the hydrophilic organic solvent, in relation to the total weight of the agent, is included in an amount of from about 20 to about 40% by weight.

13. The method according to claim 8 comprising the step of leaving the antiperspirant cosmetic agent on the skin for at least about 2 hours.

14. The method according to claim 8 comprising the step of leaving the antiperspirant cosmetic agent on the skin for at least about 4 hours.

15. The method according to claim 8 comprising the step of leaving the antiperspirant cosmetic agent on the skin for at least about 6 hours.

16. The method of claim 8, wherein the antiperspirant cosmetic agent further comprises a hydrophilic organic solvent.

17. The method of claim 8, wherein the step of applying the antiperspirant cosmetic agent to the skin comprises applying the antiperspirant cosmetic agent to the user's armpit skin.

18. An antiperspirant cosmetic agent comprising:
    a) from about 1.0 to about 10% by weight of at least one copolymer formed from at least the monomers:
        i) N-tert-octylacrylamide,
        ii) acrylic acid, and
        iii) tert.-butylaminoethyl methacrylate;
    b) from about 35 to about 55% by weight of an oil that is in liquid state at about 20° C. and about 1.013 hPa; and
    c) from about 15 to about 50% by weight of a hydrophilic organic solvent, wherein the antiperspirant cosmetic agent does not contain any aluminium-containing compounds, and wherein the oil comprises cyclopentasiloxane.

19. The antiperspirant cosmetic agent according to claim 18, wherein the copolymer a), in relation to the total weight of the agent, is included in an amount of from about 3.0 to about 7.0% by weight.

* * * * *